United States Patent [19]

Thompson

[11] Patent Number: 4,511,515
[45] Date of Patent: Apr. 16, 1985

[54] METHOD FOR MAKING A VOLATILE CERIUM DIKETONATE COMPOUND

[75] Inventor: David A. Thompson, Big Flats, N.Y.

[73] Assignee: Corning Glass Works, Corning, N.Y.

[21] Appl. No.: 508,602

[22] Filed: Jun. 28, 1983

[51] Int. Cl.$^3$ .................................................. C07F 5/00
[52] U.S. Cl. .................................................. 260/429.2
[58] Field of Search ...................... 260/429.2; 424/287

[56] References Cited

U.S. PATENT DOCUMENTS

| | | | |
|---|---|---|---|
| 3,919,274 | 11/1975 | Crisler | 260/429.1 |
| 4,036,605 | 7/1977 | Hartle | 44/68 |
| 4,133,648 | 1/1979 | Deffner | 44/68 |
| 4,176,918 | 12/1979 | Labes | 252/299.1 X |
| 4,201,721 | 5/1980 | Hallgren | 528/219 X |
| 4,206,132 | 6/1980 | Sievers | 260/429.2 |
| 4,211,535 | 7/1980 | Hartle | 44/68 |
| 4,424,165 | 3/1984 | Thompson | 260/429.2 |

FOREIGN PATENT DOCUMENTS

| | | |
|---|---|---|
| 103447 | 3/1984 | European Pat. Off. . |
| 103446 | 3/1984 | European Pat. Off. . |
| 2231289 | of 1974 | France . |

OTHER PUBLICATIONS

Rubtsov, E. M. et al., Radiokhimiya, vol. 23(4), pp. 567–574 (1981).
Pinnavaia, T. J., Diss. Abstr. B, vol. 28(1), p. 87 (1967).
Anufrieva, S. I. et al., Izv. Akad. Nauk. SSSR, Ser. Khim., vol. 7, pp. 1458–1463 (1981).
Honjo, T. et al., Bull. Inst. Chem. Res., Kyoto Univ., vol. 55(5), pp. 423–428 (1977).
Ciampolini, M. et al., J. Chem. Soc., Dalton Trans., vol. 14, pp. 1325–1328 (1977).
Fay, Robert C. et al., J. Am. Chem. Soc., vol. 101(5), pp. 1115–1122 (1979).
Anufrieva, S. I., Deposited Doc., VINITI 3167–3181, pp. 78–80 (1981), Russ.
Spitsyn, V. I. et al., Izv. Akad. Nauk. SSSR, Ser. Khim., vol. 4, pp. 772–777 (1982).
Thompson D. A., Disser. Abst. Int., vol. 38(3), p. 1199 (1977).
Wiedenheft, C. J., Inorg. Nucl. Chem. Lett., vol. 7, pp. 439–442 (1971).
Fontaine, R. et al., Chromatographia, vol. 3(11), pp. 532–533 (1970).
Swain, H. A. et al., Inorg. Chem., vol. 9(7), pp. 1766–1769 (1970).
Martin-Rovet, D. et al., J. Inorg. Nucl. Chem., vol. 43 (6), pp. 1227–1229 (1981).
Folcher, G. et al., Can. J. Chem., vol. 55(20), pp. 3559–3561 (1977).
Smith, W. J. et al., Inorg. Chem., vol. 16(12), pp. 3008–3012 (1977).
Weidenheft, C. J., Inorg. Chem., vol. 8(5), pp. 1174–1179 (1969).
Robert E. Sievers et al., "Volatile Metal Complexes", *Science*, vol. 201, Jul. 21, 1978, pp. 217–223.

Primary Examiner—Leland A. Sebastian
Assistant Examiner—M. Moskowitz
Attorney, Agent, or Firm—K. van der Sterre

[57] ABSTRACT

A method for the synthesis of tetrakis-(6,6,7,7,8,8,8,-heptafluoro-2,2-dimethyl-3,5-octanedione) cerium (IV), [Ce(fod)$_4$] wherein the product is directly formed by reacting the deprotonated beta-diketonate ligand with a cerium (IV) salt, is disclosed.

3 Claims, 1 Drawing Figure

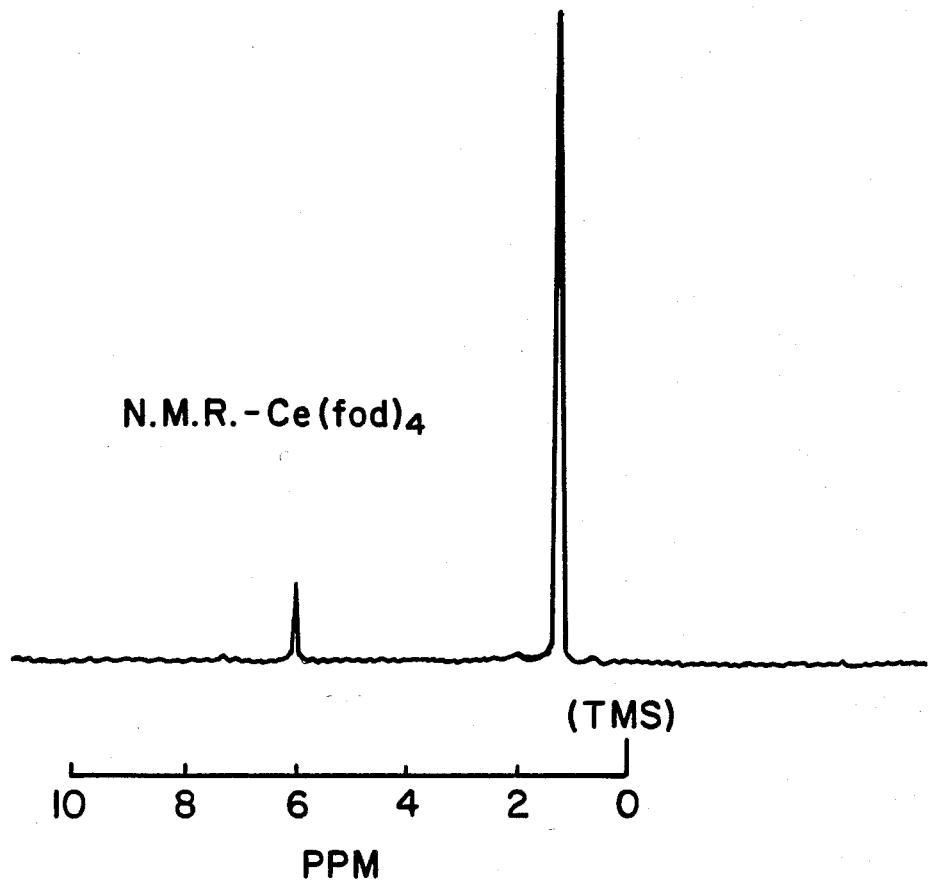

METHOD FOR MAKING A VOLATILE CERIUM DIKETONATE COMPOUND

BACKGROUND OF THE INVENTION

The present invention relates to organometallic compounds and particularly to a method for making a complex of cerium (IV) with the β-diketone dimethyl heptafluorooctanedione which exhibits unusually high volatility and stability.

Volatile metal complexes are of interest for a variety of applications, including use as fuel additives, metal vapor sources for vapor phase reactions, and gas transport reagents. A useful discussion of β-diketonate complexes and their uses is provided by R. E. Sievers et al. in Science, 201 [4352], pages 217–223 (July 1978), wherein numerous references to the preparation and use of these complexes are cited.

β-diketonates of the rare earth or lanthanide series of elements of the Periodic Table have the general formula Ln(AA')$_3$, wherein Ln is the metal element and AA' represents the diketonate ligand which forms the complex. Discussions of the synthesis and properties of the rare earth β-diketonate complexes usually do not treat the cerium complexes. This is due to the complexity arising because cerium has two stable oxidation states.

The trivalent paramagnetic complexes of Ce$^{III}$ with β-diketonates such as acetylacetone [Ce(acac)$_3$], trifluoroacetylacetone [Ce(tfa)$_3$], and hexafluoroacetylacetone [Ce(hfa)$_3$] are frequently mentioned but only a few tetravalent (Ce$^{IV}$) compounds have been reported. These include Ce(acac)$_4$, Ce(tfa)$_4$ and complexes of cerium with 2,2,6,6-tetramethyl-3,5-heptanedione (thd) and the aromatic diketone (C$_6$H$_5$CO)$_2$CH, the first two being made by the oxidative decomposition of trivalent complexes incorporating the same ligands in an inert solvent in flowing air or oxygen. In the case of Ce(tfa)$_4$, yields are poor even in the presence of excess quantities of the free β-diketone (Hfta).

Cerium complexes have also been formed with some of the 10-carbon β-diketones, including 6,6,7,7,8,8,8-heptafluoro-2,2-dimethyl-3,5-octanedione [Ce(fod)$_3$] and 2,2,7-trimethyl-3,5-octanedione [Ce(tod)$_4$]. However, none of these cerium complexes have exhibited sufficient stability and volatility to be truly useful as a cerium metal vapor source for vapor phase reactions designed to produce cerium-containing products.

A new cerium complex exhibiting high volatility and good stability at volatilization temperatures is disclosed in my copending, commonly assigned patent application, Ser. No. 418,216 filed Sept. 15, 1982. This compound, referred to as Ce(fod)$_4$, is the complex of cerium (IV) with the fluorinated β-diketone 6,6,7,7,8,8,8-heptafluoro-2,2-dimethyl-3,5-octanedione (abbreviated Hfod).

A process for making this diketonate complex, which is disclosed in my application, involves reacting the deprotonated diketone (fod$^-$) with a cerium (III) compound such as Ce(NO$_3$)$_3$.6H$_2$O to produce the octahedrally coordinated cerium (III) complex Ce(fod)$_4$$^{-1}$, and then slowly oxidizing this complex by stirring under oxygen to produce the cerium (IV) complex Ce(fod)$_4$. A disadvantage of this process is that the oxidation step must be carried out slowly and completely in order to avoid residual cerium (III) complex in the product.

SUMMARY OF THE INVENTION

The present invention provides a novel and improved process for producing Ce(fod)$_4$ which avoids the time consuming oxidation step. It is found that the desired cerium (IV) complex can be formed immediately and quantitatively by reacting the deprotonated diketone (fod$^-$) with a soluble cerium (IV) compound such as a cerium (IV) salt. Convenient sources of dissolved cerium (IV) salts are soluble inorganic cerate complexes. For example, cerium (IV) nitrate can be obtained from the (NH$_4$)$_2$Ce(NO$_3$)$_6$ complex ammonium hexanitrato cerate.

The reaction of the dissolved salt with the deprotonated diketone immediately produces the desired Ce(fod)$_4$ complex. The product is essentially free of cerium (III) complexes such as Ce(fod)$_4$$^{-1}$.

BRIEF DESCRIPTION OF THE DRAWING

The drawing consists of an $^1$H nmr spectrum of a sample of Ce(fod)$_4$ synthesized in accordance with the invention.

DETAILED DESCRIPTION

Ce(fod)$_4$ offers significant advantages over prior art β-diketonate complexes of cerium with respect to both thermal stability and volatility. It has a vapor pressure at least 2 orders of magnitude higher than that of the cerium (III) complex with the same ligand, Ce(fod)$_3$. Also, it is stable against decomposition at temperatures sufficiently high to permit vapors of the compound to be efficiently generated at substantial partial pressures. Thus the compound is believed to be superior to previous cerium compounds when used, for example, as a vapor source of cerium in a chemical vapor deposition reaction.

Generally, cerium β-diketonate complexes of Hfod are produced by the deprotonation of the diketone at the C4 position to produce (fod)$^-$ anions or ligands. Four of these ligands then combine with a cerium ion to form a complex wherein the metal is in 8-fold coordination with the oxygen atoms in the ligands.

The method of synthesis employed to produce Ce(fod)$_4$ in the aforementioned commonly assigned patent application involved reacting the deprotonated ligand (fod$^-$) with a cerium (III) compound. This procedure is illustrated by the following example.

EXAMPLE 1

Old Synthesis

A 68.2 g sample of the β-diketone 6,6,7,7,8,8,-heptafluoro-2,2-dimethyl-3,5-octanedione (Hfod) is added to 115 ml of 2M aqueous NH$_4$OH resulting in a white precipitate which is separated and dissolved in a mixture of 200 ml of water and 200 ml of methanol. The resulting solution is placed in an addition funnel and is added dropwise to a nitric acid solution of cerium nitrate, the latter solution being made by adding 25.0 g Ce(NO$_3$)$_3$.6H$_2$O to 60 ml of 1.4M NHO$_3$. After addition of the water-methanol solution, 2M NH$_4$OH is added to the reaction mixture to achieve and maintain a pH of 6.

The resulting mixture separates into a red oil phase and an aqueous phase. The phases are stirred together under oxygen at room temperature to obtain complete oxidation of Ce$^{+3}$ to Ce$^{+4}$. This requires about 24 hours. Thereafter, hexanes (200 ml) are added and the hexane layer containing the product is separated from the aqueous phase, filtered, and evaporated to dryness in a rotary evaporator.

The red solid is redissolved in 300 ml of hexanes and 600 ml of ethanol is added. Crystals of red Ce(fod)$_4$ form after cooling of the solution. However, unless care is exercised during the oxidation step, it is possible that cerium (III) complexes may be retained in the product. This is undesirable because these complexes are generally less stable and volatile than Ce(fod)$_4$.

Cerium (IV) salts which can be used to produce the Ce(fod)$_4$ complex in accordance with the present invention include the nitrate, sulfate and perchlorate salts of Ce$^{+4}$. These are not handled directly, but are instead produced by dissolving complex cerate salts or acids in aqueous acidic solutions, e.g., solutions of HNO$_3$ or other mineral acids.

Among the cerate complexes which could be used as cerium (IV) sources are (NH$_4$)$_2$Ce(NO$_3$)$_6$, (NH$_4$)$_4$Ce(SO$_4$)$_4$·2H$_2$O, H$_4$Ce(SO$_4$)$_4$, and H$_2$Ce(ClO$_4$)$_6$. However, cerium (IV) nitrate solutions produced from the (NH$_4$)$_2$Ce(NO$_3$)$_6$ starting material are presently preferred because they are anhydrous salts and are available in substantially higher purity (being essentially free of iron or other rare earth elements) than the other cerium (IV) starting materials.

As illustrated by the following Example, the method of the present invention avoids the oxidation step necessary to convert the cerium (III) complex, and thus provides a more rapid and convenient synthesis.

EXAMPLE 2

New Synthesis

A 15.4 gram sample of ceric ammonium nitrate (ammonium hexanitrato cerate), (NH$_4$)$_2$Ce(NO$_3$)$_6$) is dissolved in 25 ml of 1.4M nitric acid with vigorous stirring to form a ceric nitrate solution. A primary standard certified grade of this cerate, commercially available from the G. F. Smith Chemical Co., Columbus, Ohio, is used.

In a separate flask, 34.2 grams of 6,6,7,7,8,8,8-heptafluoro-2,2-dimethyl-3,5-octanedione (Hfod) is mixed with 75 ml of 2M NH$_4$OH to give a white precipitate of NH$_4$fod. This white precipitate is dissolved in about 200 ml of methanol to form a ligand solution.

The ligand solution thus prepared is slowly added to the ceric nitrate solution with stirring, and a red complex of the desired Ce(fod)$_4$ product is immediately formed. After stirring for 2 hours at room temperature the product is separated from the reaction mixture by filtration and dried in a vacuum. The yield is quantitative. Additional purification by recrystallization from hexane-ethanol or sublimation is possible if desired.

The identity of the product is confirmed by $^1$H nuclear magnetic resonance spectrum to be the desired Ce(fod)$_4$. The drawing consists of an $^1$H nmr spectrum at 60 MHz of this product in a CCl$_4$ solvent against a tetramethylsilane standard. The spectrum shows no evidence of the byproduct Ce(fod)$_4^{-1}$.

The very low melting point of Ce(fod)$_4$, e.g., about 97° C., is a particular advantage where the compound is to be used to supply cerium-containing vapors for a vapor phase reaction. Other cerium complexes such as Ce(tod)$_4$ and Ce(tfa)$_3$ exhibit significantly higher melting points, e.g., 134° C. and 176° C., respectively. Ce(fod)$_4$ also exhibits significantly higher volatility and thermal stability than many other trivalent and tetravalent cerium $\beta$-diketonates.

Of course the foregoing example is merely illustrative of the invention and it will be recognized that numerous variations and modifications of the specific procedures hereinabove described may be resorted to by those skilled in the art within the scope of the appended claims.

I claim:

1. A process for the synthesis of tetrakis-(6,6,7,7,8,8,8-heptafluoro-2,2-dimethyl-3,5-octanedione) cerium (IV) which comprises the steps of:
   (a) preparing an aqueous solution of a soluble cerium (IV) salt, to provide a cerium (IV) solution; and
   (b) combining the cerium (IV) solution with deprotonated 6,6,7,7,8,8,8-heptafluoro-2,2-dimethyl-3,5-octanedione to react the octanedione with the cerium (IV), and to thereby yield a tetrakis-(6,6,7,7,8,8,8-heptafluoro-2,2-dimethyl-3,5-octanedione) cerium (IV) product.

2. A process in accordance with claim 1 wherein the cerium (IV) salt is cerium (IV) nitrate.

3. A process in accordance with claim 2 wherein the cerium (IV) nitrate is produced by dissolving (NH$_4$)$_2$Ce(NO$_3$)$_6$ in an acidic medium.

* * * * *